(12) United States Patent
Regala et al.

(10) Patent No.: US 10,363,139 B2
(45) Date of Patent: Jul. 30, 2019

(54) BALL AND SOCKET ASSEMBLY

(71) Applicant: MOXIMED, INC., Hayward, CA (US)

(72) Inventors: Alan C. Regala, Mountain View, CA (US); Clinton N. Slone, San Francisco, CA (US); Michael E. Landry, Austin, TX (US)

(73) Assignee: MOXIMED, INC., Fremont, CA (US)

( * ) Notice: Subject to any disclaimer, the term of this patent is extended or adjusted under 35 U.S.C. 154(b) by 718 days.

(21) Appl. No.: 14/863,663

(22) Filed: Sep. 24, 2015

(65) Prior Publication Data

US 2016/0128835 A1     May 12, 2016

Related U.S. Application Data

(62) Division of application No. 12/112,186, filed on Apr. 30, 2008, now Pat. No. 9,168,065.

(51) Int. Cl.
*A61F 2/32*     (2006.01)
*A61F 2/30*     (2006.01)
(Continued)

(52) U.S. Cl.
CPC ............... *A61F 2/30* (2013.01); *A61B 17/68* (2013.01); *A61F 2/30744* (2013.01); *A61F 2/32* (2013.01); *A61F 2/3804* (2013.01); *A61F 2/4202* (2013.01); *A61F 2/4225* (2013.01); *A61F 2/4241* (2013.01); *A61B 17/6425* (2013.01); *A61F 2/08* (2013.01); *A61F 2/34* (2013.01); *A61F 2/38* (2013.01); *A61F 2002/30301* (2013.01); *A61F 2002/30604* (2013.01); *A61F 2002/30652* (2013.01); *A61F 2002/30654* (2013.01); *A61F 2002/30662* (2013.01); *A61F 2002/30685* (2013.01); *A61F 2002/30925* (2013.01); *A61F 2002/3453* (2013.01); *A61F 2002/3617* (2013.01);
(Continued)

(58) Field of Classification Search
CPC .................................... A61F 2/32; A61F 2/34
See application file for complete search history.

(56) References Cited

U.S. PATENT DOCUMENTS 3,493,252 A     2/1970   Watson et al.
3,575,375 A *   4/1971   Strem, Jr. ................. B60R 1/04
                                                        248/481
(Continued)

FOREIGN PATENT DOCUMENTS

EP     9383419     8/1990
EP     0953317     4/1999
(Continued)

OTHER PUBLICATIONS

PCT search report dated Aug. 27, 2009 from PCT application No. PCT/US2009/002688 as issued by the European Patent Office as searching authority.

*Primary Examiner* — Daniel J Wiley
(74) *Attorney, Agent, or Firm* — Cermak Nakajima & McGowan LLP; Adam J. Cermak (57) ABSTRACT

A ball and socket assembly including a ball component with a notch formed therein. The socket is a one-piece structure including an opening sized to receive the ball component. The ball is a capable of being inserted into the socket when the notch, cavity, or undercut is properly oriented relative to the opening of the one-piece socket.

6 Claims, 12 Drawing Sheets

(51) Int. Cl.
  *A61B 17/68* (2006.01)
  *A61F 2/38* (2006.01)
  *A61F 2/42* (2006.01)
  *A61B 17/64* (2006.01)
  *A61F 2/08* (2006.01)
  *A61F 2/34* (2006.01)
  *A61F 2/36* (2006.01)

(52) U.S. Cl.
  CPC ............... *A61F 2002/3619* (2013.01); *A61F 2002/3623* (2013.01); *A61F 2230/0095* (2013.01); *A61F 2310/00023* (2013.01); *A61F 2310/00029* (2013.01); *A61F 2310/00179* (2013.01)

(56) References Cited

U.S. PATENT DOCUMENTS

| | | | |
|---|---|---|---|
| 3,648,294 A | 3/1972 | Shahrestani | |
| 4,279,041 A * | 7/1981 | Buchholz | A61F 2/32 403/123 |
| 4,570,625 A | 2/1986 | Harris | |
| 4,712,814 A * | 12/1987 | Petterson | F16C 11/0619 285/325 |
| 4,950,299 A * | 8/1990 | Noiles | A61F 2/32 623/22.18 |
| 4,988,349 A | 1/1991 | Pennig | |
| 5,375,823 A | 12/1994 | Navas | |
| 5,405,347 A | 4/1995 | Lee et al. | |
| 5,540,688 A | 7/1996 | Navas | |
| 5,662,648 A | 9/1997 | Faccioli et al. | |
| 5,662,650 A | 9/1997 | Bailey et al. | |
| 5,803,924 A | 9/1998 | Oni et al. | |
| 5,916,270 A * | 6/1999 | Lipman | A61F 2/32 623/22.15 |
| 6,036,691 A | 3/2000 | Richardson | |
| 6,113,637 A | 9/2000 | Gill et al. | |
| 6,162,223 A | 12/2000 | Orsak et al. | |
| 6,176,860 B1 | 1/2001 | Howard | |
| 6,264,696 B1 | 7/2001 | Reigner et al. | |
| 6,409,729 B1 | 6/2002 | Martinelli et al. | |
| 6,802,866 B2 * | 10/2004 | Bunz | A61F 2/30907 623/22.14 |
| 6,966,910 B2 | 11/2005 | Ritland | |
| 7,188,626 B2 | 3/2007 | Foley et al. | |
| 7,241,298 B2 | 7/2007 | Nemec et al. | |
| 7,252,670 B2 | 8/2007 | Morrison et al. | |
| 7,276,070 B2 | 10/2007 | Muckter | |
| 7,291,150 B2 | 11/2007 | Graf | |
| 7,335,231 B2 | 2/2008 | McLean | |
| 7,361,196 B2 | 4/2008 | Fallin et al. | |
| 7,393,362 B2 * | 7/2008 | Cruchet | A61F 2/32 623/22.18 |
| 7,455,694 B2 * | 11/2008 | Epaules | A61F 2/32 623/22.15 |
| 7,611,540 B2 | 11/2009 | Clifford et al. | |
| 7,749,277 B2 | 7/2010 | McLean | |
| 7,833,276 B2 * | 11/2010 | Auxepaules | A61F 2/32 623/22.18 |
| 8,029,571 B2 | 10/2011 | McLean | |
| 8,029,572 B2 | 10/2011 | McLean | |
| 9,168,065 B2 | 10/2015 | Regala et al. | |
| 9,168,066 B2 | 10/2015 | Regala et al. | |
| 2002/0099447 A1 | 7/2002 | Mears et al. | |
| 2002/0116068 A1 * | 8/2002 | McLean | A61F 2/32 623/22.15 |
| 2003/0191817 A1 | 9/2003 | Rambert et al. | |
| 2004/0143341 A1 | 7/2004 | McLean | |
| 2004/0267179 A1 | 12/2004 | Leman | |
| 2005/0085815 A1 | 4/2005 | Harms et al. | |
| 2005/0192674 A1 | 9/2005 | Ferree | |
| 2005/0228502 A1 * | 10/2005 | Deloge | A61F 2/32 623/22.18 |
| 2006/0064169 A1 | 3/2006 | Ferree | |
| 2006/0217815 A1 | 9/2006 | Gibbs et al. | |
| 2007/0043356 A1 | 2/2007 | Timm et al. | |
| 2007/0161993 A1 | 7/2007 | Lowery et al. | |
| 2007/0168036 A1 | 7/2007 | Ainsworth et al. | |
| 2007/0198088 A1 | 8/2007 | Biedermann et al. | |
| 2007/0198091 A1 | 8/2007 | Boyer et al. | |
| 2007/0244483 A9 | 10/2007 | Winslow et al. | |
| 2008/0097441 A1 | 4/2008 | Hayes et al. | |
| 2008/0125866 A1 | 5/2008 | McLean | |
| 2010/0234963 A1 | 9/2010 | McLean | |
| 2010/0241238 A1 | 9/2010 | McLean | |

FOREIGN PATENT DOCUMENTS

| | | |
|---|---|---|
| EP | 1847229 | 10/2007 |
| WO | WO94/06364 | 3/1994 |
| WO | WO2004/024037 | 3/2004 |
| WO | WO2006/110578 | 10/2006 |
| WO | WO2008/006098 | 1/2008 |

\* cited by examiner

BALL AND SOCKET ASSEMBLY

This application is a Divisional of, and claims priority under 35 U.S.C. § 120 to, U.S. patent application Ser. No. 12/112,186, filed Apr. 30, 2008, the entirety of which is incorporated by reference herein.

FIELD OF THE EMBODIMENTS

Various embodiments disclosed herein are directed to ball in socket assembly designs.

BACKGROUND

Many ball and socket designs have been developed in order to facilitate relative angular movement between two components. Typically, the ball and socket designs include a spherical knob that is fitted into a socket defining an interior which receives the ball. One variation of the ball and socket design includes a socket having an opening that is slightly smaller than the radius of curvature for the ball member. When the ball member is coupled with the socket, the ball member is permanently secured within the socket. Alternatively, the entry within the socket is adjustable to allow the ball member to be easily inserted into or removed from the socket.

In another variation, the external profile of the ball member is adjustable (i.e., expandable) to secure the ball member within the socket. In yet another variation, the ball member includes one or more grooves or surfaces that correspond to ridges provided on the opening rim of the socket. The ball member may be coupled to the socket if the grooves are aligned with the corresponding ridges of the socket. Once inserted, the ball member is rotated to secure the ball member within the socket.

While current designs are useful, there is a continuing need for ball and socket designs having a significant range of motion and a maximum high tolerance load surface area. Moreover, there is a need for a socket embodying significant structural integrity and reduced wear under high peak stresses while assuming a low profile.

The present disclosure address these and other needs.

SUMMARY

Briefly, and in general terms, the present disclosure is directed to a ball and socket assembly. In various aspects, the disclosed assemblies embody structure facilitating significant ranges of motion of a ball component with respect to the socket. In this regard, in contemplated approaches, deformation of the ball or socket can be avoided. Moreover, due to the particular shape of the ball component, a single piece socket is possible as is an assembly having a low profile. In particular, the ball can assume a spheroid shape. The socket captures the ball without deformation of the socket or ball to prevent the ball from being able to be pulled out of the socket during use while also providing a contact surface on the ball and socket with no separation line to minimize wear during use. Such approaches have an application across fields of art and in particular, in medical applications. In one approach, the ball component can include a notch formed by removing a volume of material from its body.

In one particular aspect, a ball and socket assembly can include a joint composed of a hook-in ball and one-piece socket design. The hook-in ball and one-piece socket are coupled together in a first orientation and operates in various other different distinct orientations. In an operational configuration, the hook-in ball and one-piece socket provide a range of motion that is not overly restrictive, but rather provide ranges of motion desired for a particular or wide ranges of applications. Depending upon the embodiment, the hook-in ball and one-piece socket joint is designed to allow a range of motion including a 360 spin degrees, about a longitudinal axis of the component, ±17.5 (35) degrees of movement along a minor axis of an opening to the socket, and ±77.5 (155) degrees of movement along a major axis of the socket opening. In one preferred approach, a 0.002 diametrical clearance between the ball component and the socket is contemplated.

The hook-in ball and one-piece socket is designed to provide a durable joint that maintains functionality over a large number of cycles. The durability of the joint is attributable to cooperation of the hook-in ball and one-piece socket. Where there are split lines on wearing surfaces, relative motion between bearing surfaces can more quickly lead to structural failure. Additionally close tolerances between moving parts are more difficult to achieve and maintain. The hook-in ball design eliminates the need to apply large forces to insert the ball into the socket, thereby avoiding an approach relying on deformation of the socket or ball component to accomplish a coupling of the members. Consequently, due to an ability to employ a substantially non-deformable socket (or ball), stresses as well as wear of the ball and socket are minimized. Additionally, the complementary design of the hook-in ball and one-piece socket provides a joint with a yield strength that is greater than the maximum stresses applied at expected maximum loads, which improves longevity of the joint.

Generally, the hook-in ball defines a notched spherical head that is coupled to a shaft. The notched portion of the spherical head is formed by removing a volume of material. The notched portion can have various shapes, sizes, or locations on the spherical head. In a preferred approach, the notch surface defines a saddle shape formed by six angled surfaces. It is also contemplated that one or more notch portions can be provided on the spherical head. The notch on the spherical head reduces the effective cross-section of a portion of the head so that the resultant hook-in ball can fit into a one-piece socket having a restricted opening. That is, the hook-in ball is only insertable into the one-piece socket when the notch on the spherical head is properly oriented relative to the opening of the socket. Thus, when constrained for motion in orientations distinct from an insertion orientation, the socket securely retains the ball component.

Another embodiment of the hook-in ball is formed of two parts, a notched spherical head coupled to a shaft and a filler component. The filler component is a volume of material that is inserted into the notch of the spherical head to form a complete sphere. In this embodiment, the notched spherical head can be inserted into a one-piece socket. The filler component is then secured within the notch of the spherical head to form the completed sphere. The filler component can be removed from the spherical head to allow disassembly of the ball component from the one-piece socket.

According to one embodiment, the one-piece socket component is composed of a socket cavity having a restricted opening and includes curved walls having interior surfaces defining a bearing surface, wherein the bearing surface further defines a contour forming a portion of a sphere. The opening to the socket has a dimension along a major axis that is configured to receive the hook-in ball. The restricted opening can assume various shapes and sizes, such as elongated, symmetrical, asymmetrical, or other shapes. Depending upon the application, the restricted opening can be shaped to accommodate different ranges of motion. For example, the restricted opening can be shaped to allow linear motion (e.g., motion in one plane), curvilinear motion (non-planar motion), and/or crossing motions (i.e., motions in planes that intersect). Optionally, certain embodiments of the one-piece socket can also include one or more cut-outs that are in communication with the socket cavity.

In a preferred embodiment, the components forming the ball and socket assembly are formed from cobalt chromium. Various coatings are also contemplated. Thus, one or more of the ball and socket components can be coated with a ceramic material.

Other features and advantages will become apparent from the following detailed description, taken in conjunction with the accompanying drawings, which illustrate by way of example, the features of the various embodiments.

DETAILED DESCRIPTION

Various of the disclosed embodiments are directed to a ball and socket assembly. In the contemplated approaches, the assembly includes a ball with a portion of a non-load bearing surface removed and a one-piece socket. The components of the assembly cooperate to provide a significant range of relative motion. Also, the assembly is configured such that it assumes a desired low profile.

The ball and one-piece socket assembly can be used in any desirable mechanical application. In a medical specific application, the assembly can be employed to completely or partially replace and/or complement the hip, finger, toe, knee, elbow, ankle or other joints. In addition, the ball and socket assembly may be used in an extra-articular mechanical energy absorbing system.

In one embodiment, the ball can define a spheroid that includes a head with a notch, cavity or undercut that is coupled to a shaft. The notched or cavitied portion of the head is formed by removing a volume of material from the head. The notched or cavitied portion can have a variety of shapes, sizes, or locations on the ball component. It is also contemplated that one or more notch, cavity or undercut portions can be provided on the head. The notch, cavity or undercut on the head reduces an effective cross-section of a portion of the head so that the ball can fit into a one-piece socket having a restricted opening without deforming the ball or socket thus creating a ball and socket assembly that can withstand substantial loads and peak stresses with minimal wear. That is, the ball is insertable into the one-piece socket when the notch, cavity or undercut on the spherical head is properly oriented relative to the opening of the one-piece socket.

Generally, the one-piece socket is composed of a socket cavity having a restricted opening. The restricted opening is smaller than an effective cross-sectional dimension of the socket cavity. In certain embodiments, the opening is shaped to restrict the range of motion of the ball component. The socket cavity has approximately the same diameter as the spherical head. The socket cavity is defined by curved walls that are shaped to receive an outer surface of the head of the ball component. In a preferred approach, the curved walls of the socket cavity form a portion of a spherical shape.

In one embodiment, the ball and socket assembly includes a ball and a one-piece socket which are coupled together in a first orientation and operates in various orientations distinct from the first orientation. In the first orientation, the notched portion of the ball is aligned with the restricted opening of the one-piece socket such that insertion is possible. The smaller effective cross-section of the notched portion of the head allows the head to be inserted through the opening of the socket cavity. Once the ball head is inserted into the socket cavity, it is rotated about (i.e., rotated around the longitudinal axis of the shaft) to secure the ball within the socket cavity. In operation, the ball is constrained so that the notched portion does not contact the inner surface of the socket cavity during the entire range of motion of the ball within the socket cavity. As a result, the ball cannot be dislocated from the one-piece socket. If a force is applied to the ball head along the longitudinal axis of the shaft, this force is absorbed by a bearing surface area of the socket cavity.

The ball and socket assembly can be made from materials such as titanium, cobalt chrome (e.g., Biodur CCM Plus), ceramic, or other durable materials that produce a minimal amount of particulate material or, if particulate material is generated, the smallest size of particulate material. Additionally, the surfaces of the ball and the one-piece socket are highly polished and can be coated with a ceramic or other material. In one embodiment, the socket cavity and the outer surface of the ball component each have a surface finish that is polished to a mirror-like finish. Additionally, the selected materials for the ball and socket cavity to embody a yield strength that is greater than the maximum stresses at maximum loading that may applied to the components. Moreover, preferably the selected materials maintain functionality of the components for over two million loading cycles.

Referring now to the drawings, wherein like reference numerals denote like or corresponding parts throughout the drawings and, more particularly to FIGS. 1A-9C, there are shown various embodiments of a ball and socket assembly. More specifically, FIGS. 1A-4B illustrate various embodiments of a hook-inball having a shaft, and FIGS. 5A-7D show various embodiments of a one-piece socket. FIGS. 8A-8C and 9A-9C depict the orientation of the ball component relative to the socket during assembly. FIGS. 10-14 include exemplary applications of the ball and socket assembly in joints within the body.

Figure 1A:
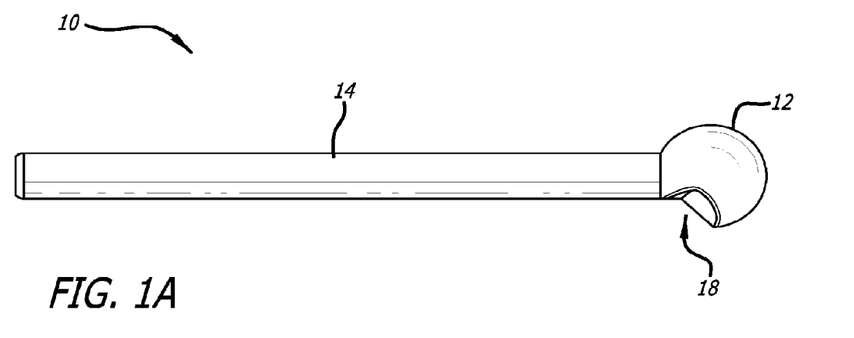
FIG. 1A is a side view of one embodiment of a ball.
Figure 1B:
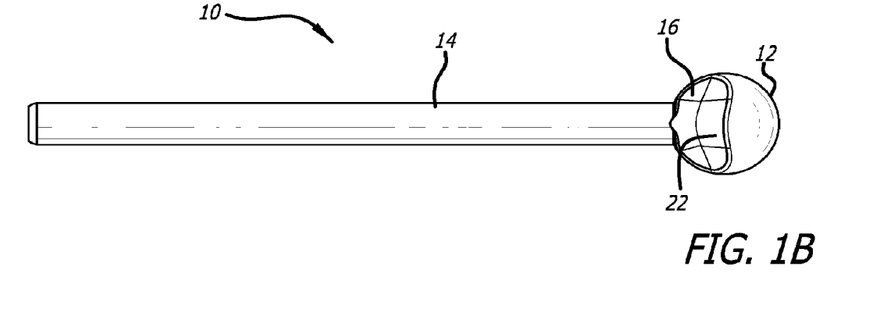
FIG. 1B is a front view of the ball shown in FIG. 1A.

Turning now to FIGS. 1A-B, a hook-in ball component 10 is composed of a ball component 12 coupled to an elongated shaft 14. The ball component 12 includes a notch, cavity or undercut 16. The ball component and the elongated shaft 14 define a unitary structure. It is contemplated, however, that the ball component and the shaft may be distinct parts that are coupled together. The notched portion 16 of the spherical head 12 results from removing a volume of material from the head. As shown in FIGS. 1A-1B, the notched portion 16 can define a generally saddle shape. In one approach, the saddle shape can be formed by six planar surfaces. Such surfaces can also have a curvature to them. The notched portion 16 on the ball head 12 reduces the effective cross-section of a portion of the head so that the head can pass through an opening formed in a socket component. As those skilled in the art will appreciate, the notched portion 16 may be any size, depth, location, or shape so long as the effective cross-section of a portion of the spherical head 12 is reduced as compared to the widest cross-section of the head. A smallest possible notch may be employed to provide a ball and socket assembly with a relatively larger interfacing surface.

The elongated shaft 14 has a diameter less than the dimension at the widest point of the spherical head 12 as shown in FIGS. 1A-1B. It is contemplated that the shaft may have any length, shape, diameter (variable or constant) depending upon the intended application.

Figure 2A:
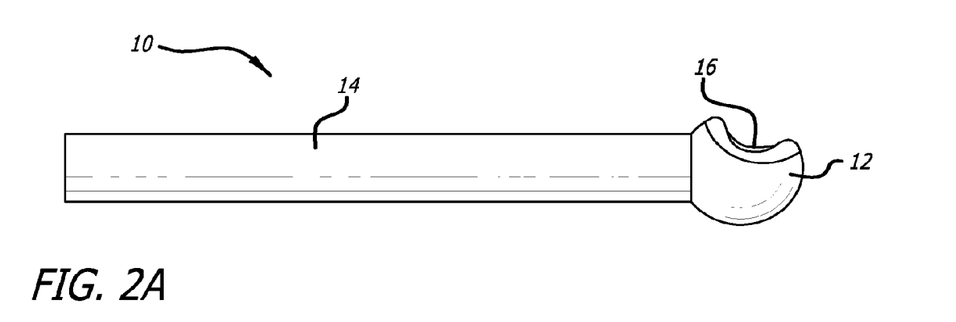
FIG. 2A is a side view of another embodiment of a ball.
Figure 2B:
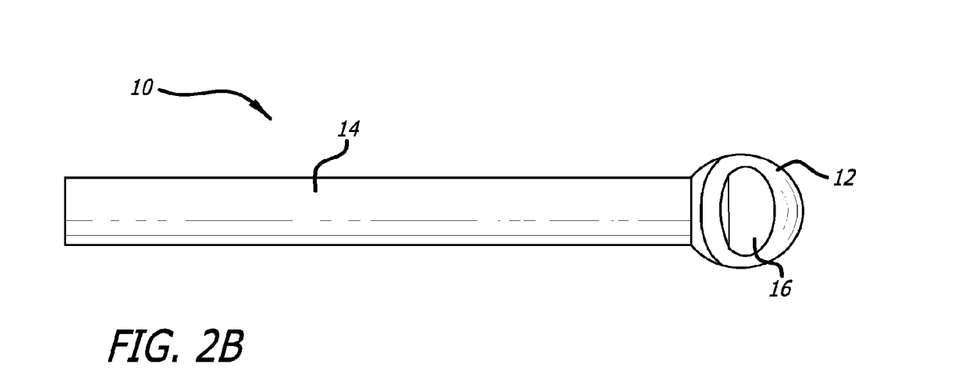
FIG. 2B is a front view of the ball shown in FIG. 2A.
Figure 2C:
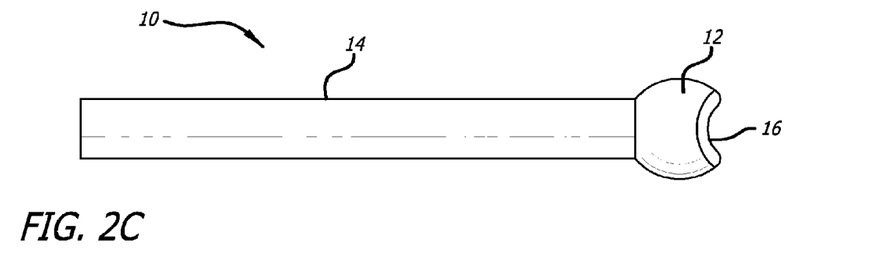
FIG. 2C is a side view of a further embodiment of a ball.
Figure 2D:
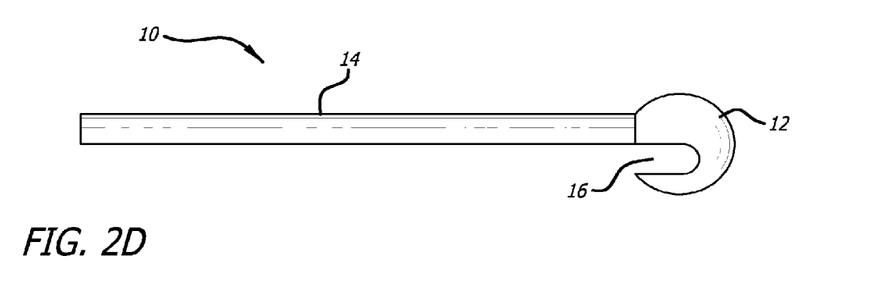
FIG. 2D is a side view of yet another embodiment of a ball.

FIGS. 2A-2D illustrate other embodiments of a ball socket assembly. As shown in FIGS. 2A-2B, a hook-in ball socket component 10 can have a notched spherical head 12 and an elongated shaft 14. Here, the notched portion 18 is defined by a concave surface formed in a side of the head of the ball component. It is contemplated that the head 12 can include one or more such notched portions 18 which can be located anywhere on the spherical head 12 for desired purposes. For example, see FIG. 2C which depicts a notched portion 16 of the spherical head 12 that is located approximately along a longitudinal axis running through the component. Again, in other embodiments, the notched portion 16 (i.e., centered or off-axis) is positionable anywhere on the surface of the head 12 so long as a portion of the head has a reduced diameter. In this regard, reference is made to FIG. 2D, where the ball component 12 includes a notch 16 having an opening directed generally parallel to shaft 14.

Figure 3A:
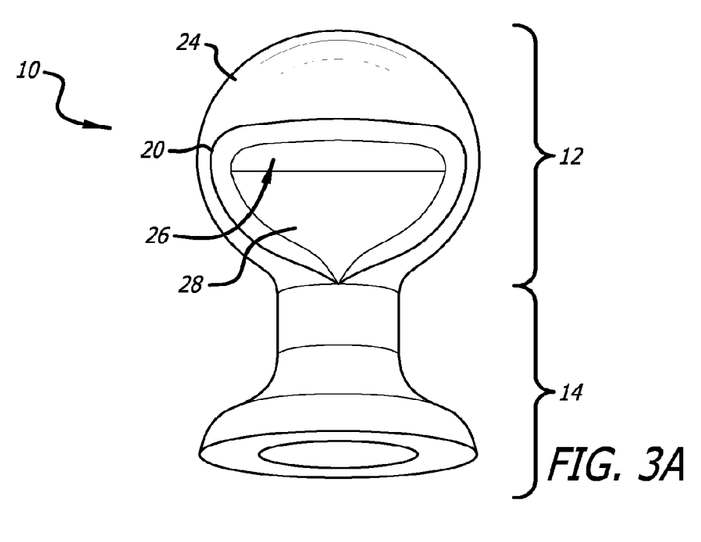
FIG. 3A is a side view of another embodiment of a ball.
Figure 3B:
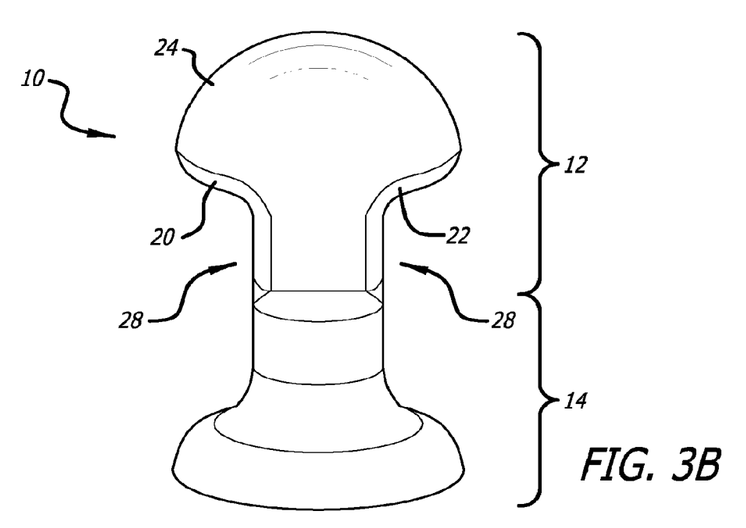
FIG. 3B is a front view of the ball shown in FIG. 3A.

FIGS. 3A-3B illustrate yet another embodiment of a ball component 10 having a notched head 12 and a shaft 14. As best shown in FIG. 3B, a notched portion 20, 22 extends to opposite sides of the head 12. Portion 24 of the head 12 forms a surface for engaging a socket component.

As shown in FIG. 3A, the notched portion 20 includes two surfaces 26, 28 that are angled with respect to one another. A first surface 26 of the notched portion 20 can be formed generally perpendicular to a longitudinal axis of the shaft 14, and a second surface 28 can approach generally parallel relatively with a longitudinal axis extending through the component. In one embodiment, the notched portion 20, 22 is dimensioned approximately equal to the outer diameter of the shaft 14 along a longitudinal dimension. Alternatively, the dimension of the notched portion 20, 22 is greater than the outer diameter of the shaft 14.

Figure 4A:
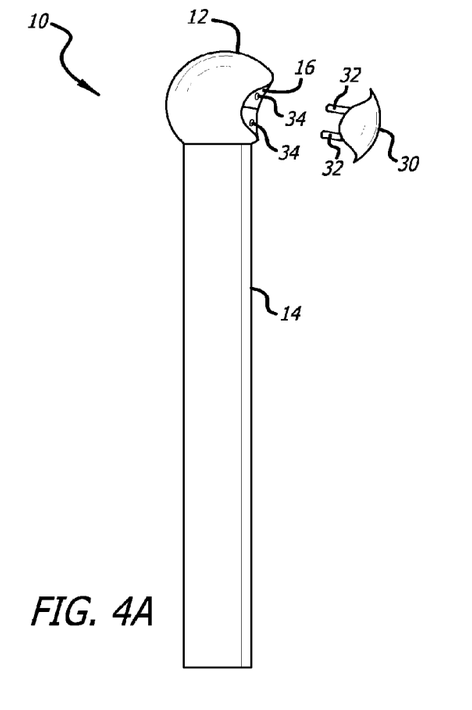
FIG. 4A is an exploded side view of another embodiment of a component ball.
Figure 4B:
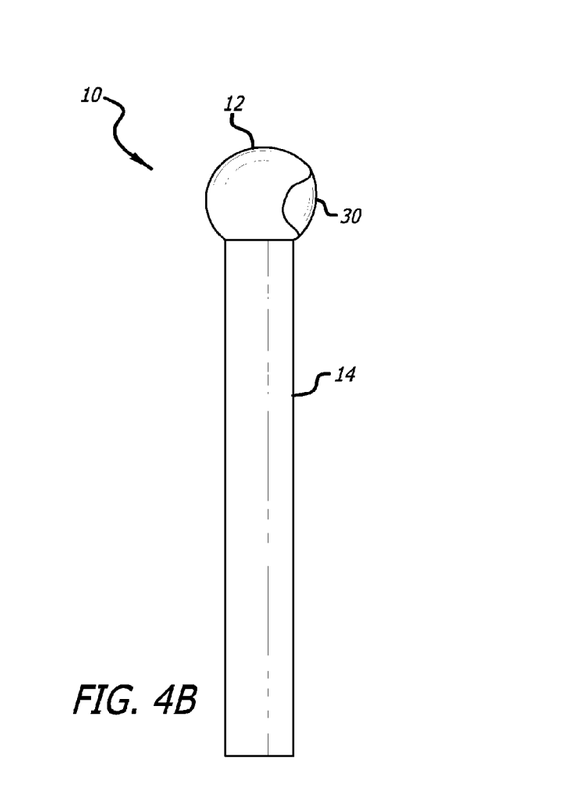
FIG. 4B is a side view of the component ball of FIG. 4A in an assembled state.

FIGS. 4A-4B illustrate another embodiment of a ball component 10. The ball component includes a notched head 12 fixed to or otherwise forms an integral unit with a shaft 14. As depicted in FIG. 4A, the head 12 has a cavity or notched portion 16 having a plurality of openings 34 positioned on the surface of the notched portion. A filler component 30 is further provided. The filler component 30 is a volume of material that is shaped and sized to mate with the notched portion 16 of the head 12. The filler component 30 includes a plurality of prongs 34 that extend away from a surface of the filler component. The prongs 34 are sized, shaped, and positioned on the filler component 30 to be press fitted into the openings 34 on the notched portion 16. A completely spherical head is formed when the filler component 30 is coupled to the notch portion 16 as depicted in FIG. 4B. The filler component 30 is inserted into the notched spherical head 12 after the head is inserted into a socket. In this way, the two piece ball component can be placed within a socket having a relatively small opening and a relatively large bearing surface. In one embodiment, the filler component 30 is reversibly inserted into the head 12 (i.e., the filler component is removable). Alternatively, it is possible that the filler component 30 may be permanently fixed to the notched spherical head 12.

Figure 5A:
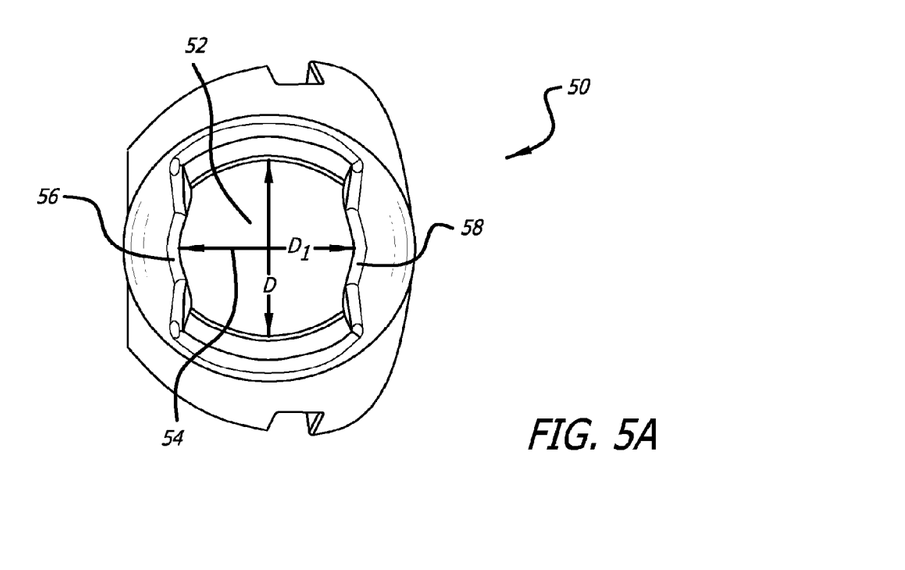
FIG. 5A is a top view of one embodiment of a one-piece socket.
Figure 5B:
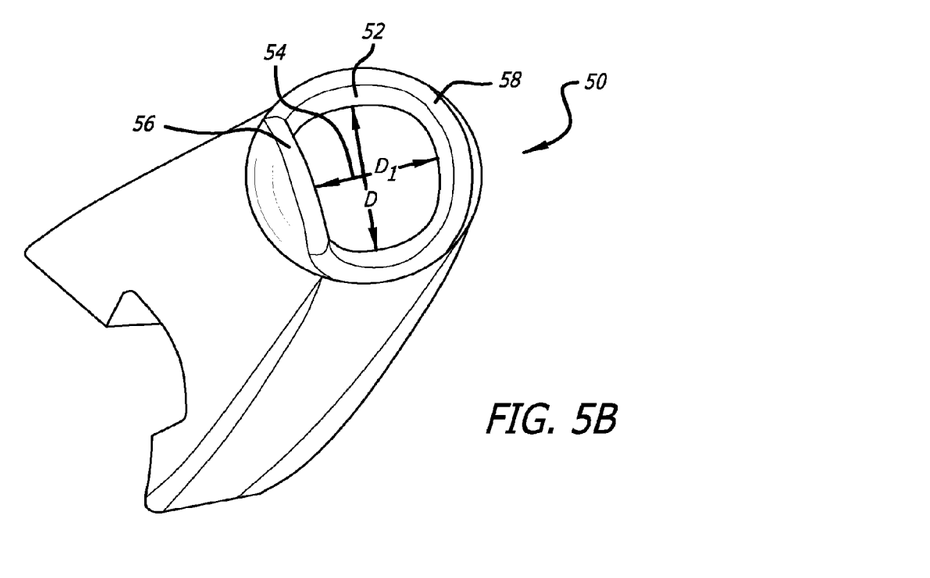
FIG. 5B is a top view of another embodiment of a one-piece socket.

Turning now to FIGS. 5A-7D, various embodiments of a socket component are shown. More specifically, FIG. 5A depicts a one-piece socket 50 having a socket cavity 52 and an opening 54 for accessing the socket cavity. The socket cavity 52 includes a contiguous surface that defines a spherical space. As shown in FIG. 5A, the socket cavity 52 has an opening having a major axis dimension D and a minor axis dimension $D_1$. Thus configured, the socket cavity is able to secure a hook-in ball component 10 having a notched head 12 with an effective minimum cross-sectional dimension which can be received within the dimensions of the major and minor axis. The ball head 12 and the socket cavity 52 are similarly dimensional in order to prevent the translation (side to side movement) of the head within the socket cavity. For example, the socket cavity 52 can have tolerances of approximately 0.002" diametrical clearance with the ball (nominal), approximately 0.0005" on ball diameter, and approximately 0.0002" on sphericity.

As stated, the opening 54 of the one-piece socket has a minor axis dimension $D_1$ that is smaller than the diameter D of the socket cavity. As a result, a completely spherical ball having a diameter D would not be insertable into the socket cavity 52 without exerting a large force that would cause deformation of the opening 54 or to the surface of the ball component. In order to avoid this situation, the ball component includes a notched portion (see FIGS. 1A-4A), which reduces the effective cross-section of a portion of the ball, so that it can pass through the opening and be secured within the socket cavity 52. The opening 54 includes structures 56, 58 which define the shape of the opening. This structure 56,58 can be symmetrical or alternatively, asymmetrical in shape.

The opening 54 and walls defining the socket secure a ball component (not shown) within the socket cavity 52 without overly restricting the range of motion. For example, the socket geometry allows 360 degrees of "spin" rotation, up to or greater than 35 degrees of motion of the ball component along the minor axis of the opening and up to or greater than 77.5° of motion of the ball component along a major axis of the opening. As those skilled in the art will appreciate, the range of motion may be restricted or expanded based upon the intended application so that degrees of matter in X, Y or Z axes can be configured as necessary.

Figure 6:
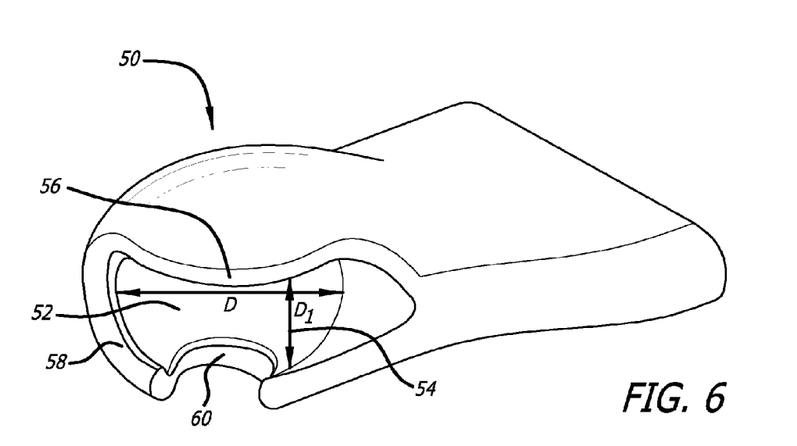
FIG. 6 is a perspective view of one embodiment of a one-piece socket having a cut-out.

FIG. 6 depicts another embodiment of a one-piece socket 50. The socket 50 includes a socket cavity 52 with a bearing surface having a dimension D and an opening having a dimension $D_1$, wherein $D>D_1$. The shape of the opening 54 is defined by the wall structures 56, 58. As shown in FIG. 6, one portion of the structure 58 includes a cut-out 60 that extends into the socket cavity 52. It is contemplated that the size, shape, and location of the cut-out 60 may be varied from FIG. 6.

Figure 7A:
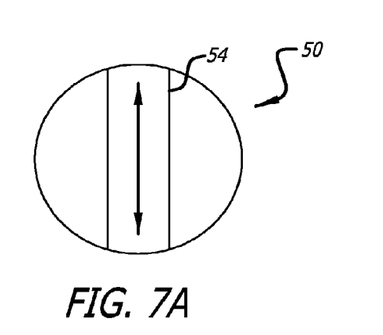
FIGS. 7A-D are top views of one-piece sockets having different ranges of motion.
Figure 7B:
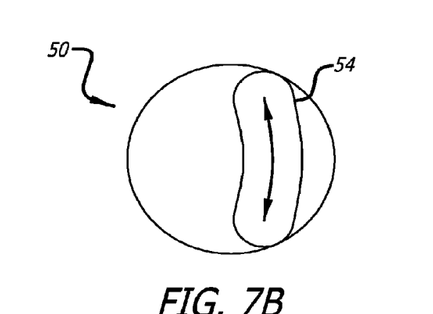
Figure 7C:
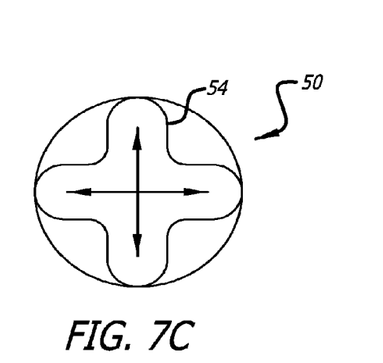
Figure 7D:
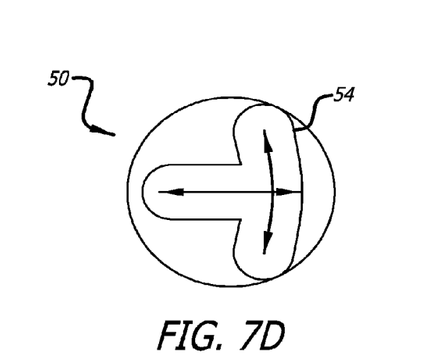

With reference to FIGS. 7A-7D, a number of sockets 50 are shown having variously shaped openings 54 that define the directions of the range of motion. FIG. 7A depicts a socket 50 having an elongated opening 54 that defines a linear motion (i.e., motion in one plane). FIG. 7B shows a one-piece socket 50 having a curved opening 54 that defines a curvilinear motion. FIG. 7C illustrates a socket 50 having an X-shaped opening 54 that defines a crossing motion (i.e., linear motions in intersecting planes). FIG. 7D shows a one-piece socket 50 having an intersecting curved opening 54 that defines a curved crossing motion (i.e., non-linear motions in intersecting planes).

Figure 8A:
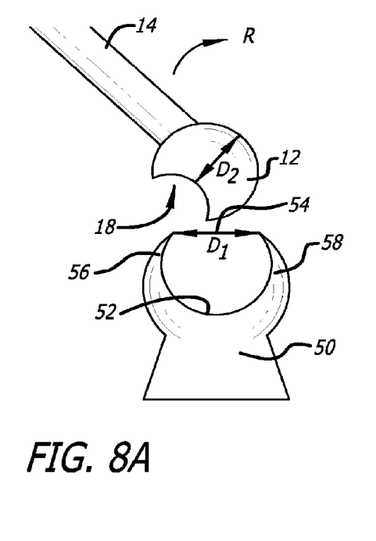
FIGS. 8A-B illustrate the orientation of the ball relative to one-piece socket when inserting the ball and after placement within the one-piece socket.
Figure 8B:
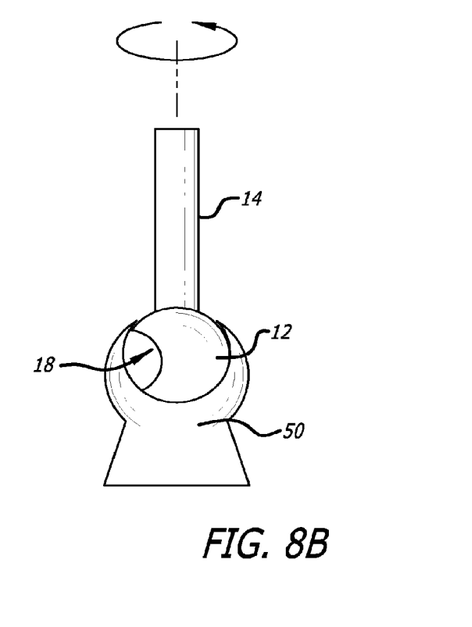
Figure 8C:
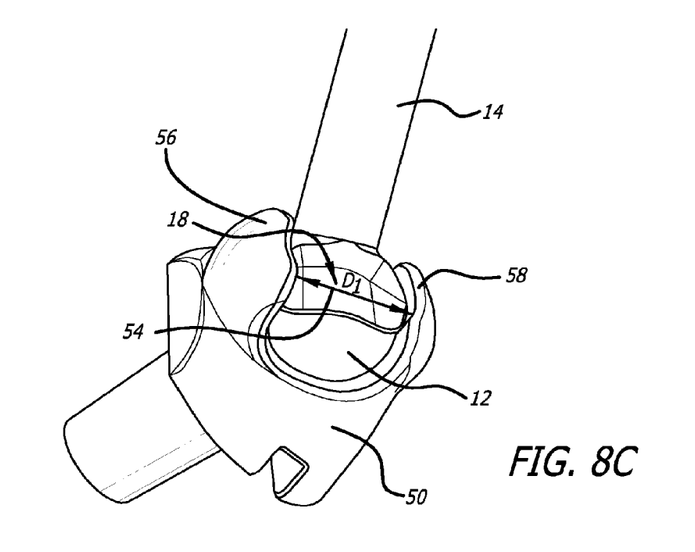
FIG. 8C illustrates the orientation of the ball relative to the one-piece socket when the ball and one-piece socket are in an operational configuration.

With reference to FIGS. 8A-8C, one exemplary method of inserting and locking of a hook-in ball in a one-piece socket is shown. As shown, the notched head 12 is oriented such that the portion of the head having the dimension $D_2$ is oriented over the opening (having a dimension $D_1$) of the socket 50. The cross-sectional dimension $D_2$ of the head 12 needs to be smaller than the dimension $D_1$ of the restricted opening in order for the notched head to be inserted through the restricted opening. As shown in FIG. 8A, the notched portion 18 straddles a perimeter structure 56 of the restricted opening, and the shaft 14 is rotated in direction R to insert the head 12 into the socket cavity 52.

FIG. 8B shows the head 12 of the hook-in ball positioned within the socket cavity 52 of the socket. The hook-in ball is rotated about the longitudinal axis of the shaft 14 in order to secure the hook-in ball within the socket cavity 52. The notched head 12 only needs to be slightly rotated to be secured within the socket cavity. For example, but not by of limitation, the spherical head 12 can be rotated 5°-10° to secure the head 12 within the cavity 52. In an engaged orientation, it is contemplated that pull forces of at least 260 lbs is required to separate the head 12 from the socket cavity 52. Additionally, as shown in FIG. 8C, the notched portion 18 is oriented such that it faces away from contact with the socket cavity 52 surface when a longitudinal load along the axis of the shaft 14 is applied to the spherical head. Stated differently, when a load is applied to the joint, the contact area between the spherical head 12 and the socket cavity 52 consists of the a curved portion of the head and the bearing surface of the socket cavity.

Figure 9A:
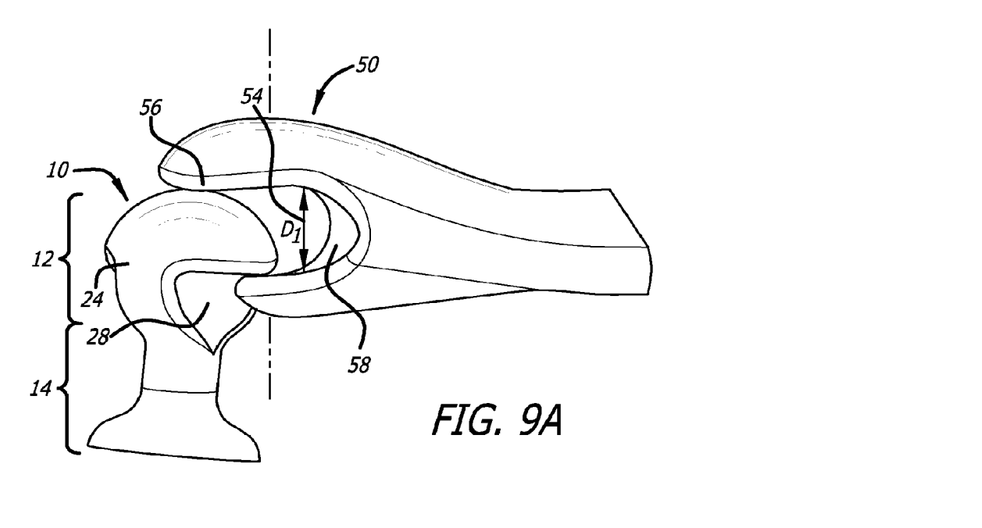
FIGS. 9A-C illustrate the coupling and operational orientations of the ball shown in FIGS. 3A-B and the one-piece socket shown in FIG. 7.
Figure 9B:
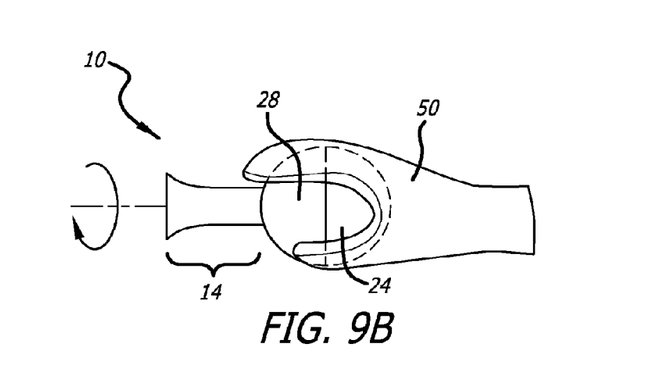
Figure 9C:
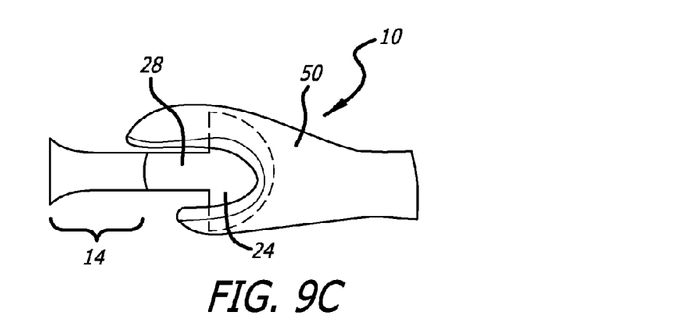

FIGS. 9A-9C illustrate another exemplary method of inserting and locking of another embodiment of a hook-in ball 10 within socket 50. A longitudinal axis of the hook-in ball 10 is first aligned generally perpendicular to the socket cavity 50 as shown in FIG. 9A. As such, the hook-in ball 10 is oriented so that the notched portions 20, 22 are inserted into the cut-out portion 60. Also, a top of the head 24 is inserted into the opening 54. Once the top portion of the head has been inserted through the opening 54, the hook-in ball 10 is rotated approximately 90° in direction R to the configuration shown in FIG. 9B. The hook-in ball 10 may be secured within the socket cavity by rotating the hook-in ball a few degrees or as much as 90°.

Figure 10:
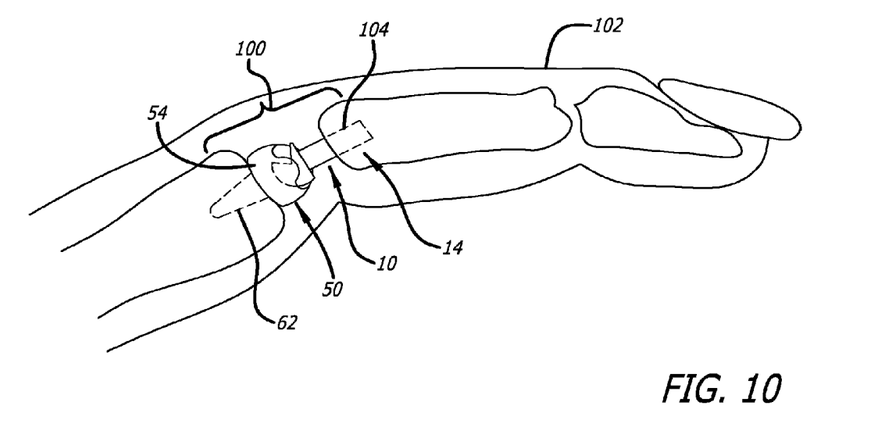
FIG. 10 illustrates one embodiment of a ball and socket assembly as a joint prosthesis for a finger joint.

Referencing FIGS. 10-14, various applications of the hook-in ball and socket assemblies 100 are depicted. As shown in FIG. 10, the assembly 100 is used in a finger 102. A stem 62 of the socket 50 is inserted into an end of bone (e.g., metacarpal bone). As shown in FIG. 10, the stem 62 has a tapered diameter, but it is contemplated that the stem may have a constant outer diameter. Optionally, the stem 62 may be etched, roughened, or coated with osteointegrating materials. The opening of the socket 54 is generally shaped to allow the natural range of motion of the finger joint (i.e., flexion and extension in a plane). The geometry of the opening can be modified from a linear motion to a curvilinear motion or cross trajectories for the thumb or other multi-axial joints within the body.

The hook-in ball 10 of the assembly 100 may be attached on an opposite side of the joint such as by inserting a shaft 14 into the end of the other bone of the joint (e.g., proximal phalanges). Like the stem 62 of the socket 50, the shaft 14 of the hook-in ball may have a variable or constant diameter or an osteointegration surface provided on the outer surface. Optionally, the shaft 14 includes a keel 104 that extends away from the outer diameter of the shaft of the hook-in ball. Additionally, the keel 104 may be provided on the stem 62 of the socket 50. The keel 104 stabilizes the hook-in ball 10 or the socket 50 by preventing rotation of these components.

The use of the hook-in ball and socket assembly 100 as a finger joint prosthesis decreases the rate of joint dislocation as the pull out forces required to remove the hook-in ball from the socket cavity are very large. Additionally, the assembly 100 is made of materials such as, but not limited to, titanium, cobalt chrome, or stainless steel which have increased durability as compared to silicone or polymeric prosthesis. Additionally, the assembly 100 has improved stability as compared to other finger joint prosthesis.

The hook-in ball and socket assembly 100 may be used in any of the finger joints (e.g., between carpals and metacarpals, between the proximal phalanges and middle phalanges, or the middle phalanges and the distal phalanges). In another application, the assembly 100 may be used to partially or completely replace toe joints.

Figures 11A, 11B:
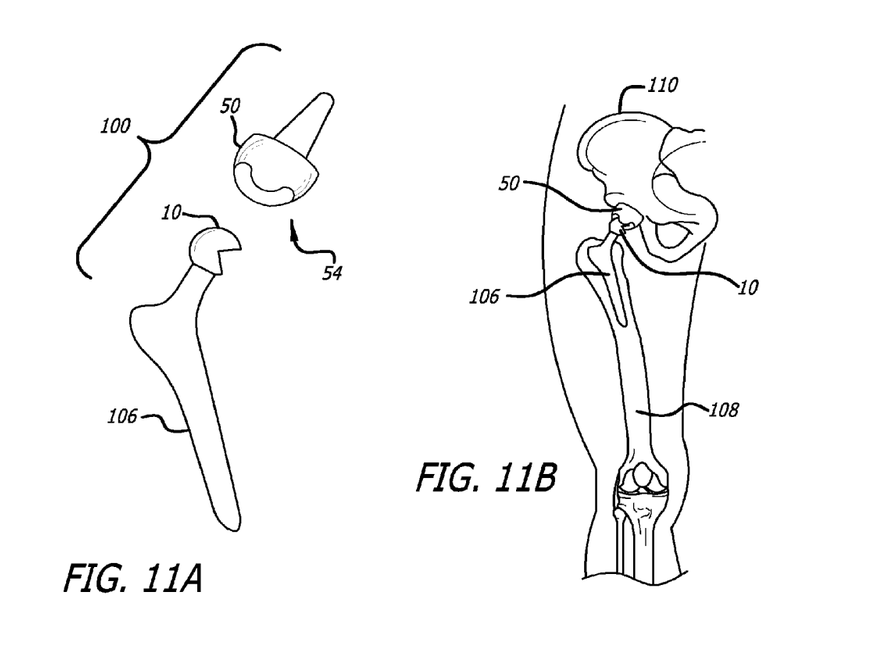
FIGS. 11A-B illustrates one embodiment of a ball and socket assembly as a joint prosthesis for a hip joint.

FIGS. 11A-11B illustrate the use of the hook-in ball and socket assembly 100 as a hip joint prosthesis. As shown in FIG. 11A, a hook-in ball 10 is coupled to a body extension 106. The hook-in ball 10 and body extension 106 are coupled to the femur 106 as shown in FIG. 11B. Alternatively, only the hook-in ball 10 component is used to replace the head of the femur 106. The socket 50 is used to replace the natural hip socket in the pelvic bone 110. As described above, the hook-in ball 10 and the socket 50 can include osteointegration surfaces, keels, or other stabilizing structures. The use of the hook-in ball and socket assembly 100 decreases the rate of joint dislocation as the pull out forces required to remove the hook-in ball 10 from the socket 50 are very large. Additionally, the geometry of the socket opening can be shaped to provide limited/controlled excursion of the hook-in ball within the socket.

Figure 12:
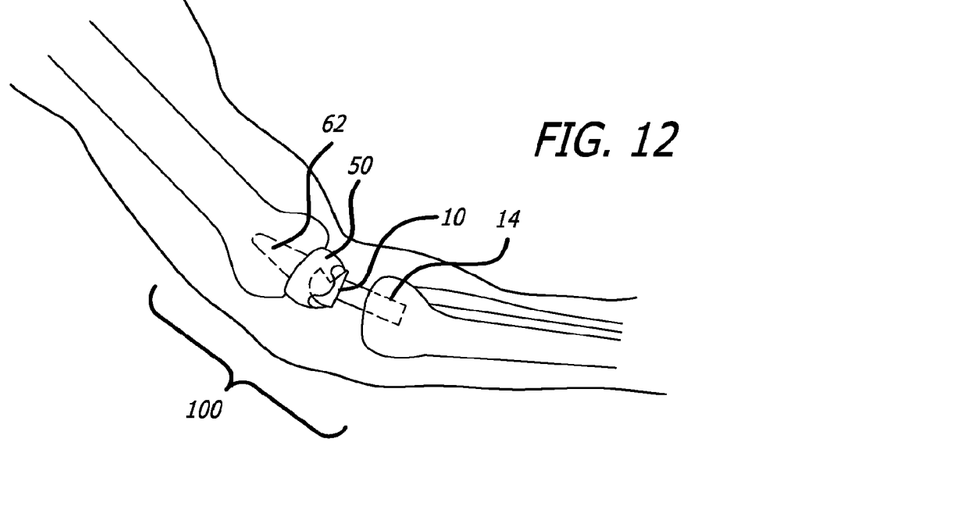
FIG. 12 illustrates one embodiment of a ball and socket assembly as a joint prosthesis for an elbow joint.

FIG. 12 illustrates the use of the hook-in ball 10 and socket 50 assembly as an elbow joint prosthesis. Similar to the other joint prostheses previously disclosed, the use of the hook-in ball 10 and the socket 50 can reduce the rate of dislocation of the joint. Additionally, as an elbow joint prosthesis, the hook-in ball and one-piece socket joint 100 eliminates the need for the radius bone since the assembly 100 can rotate as well as translate to approximate natural motion.

Figure 13:
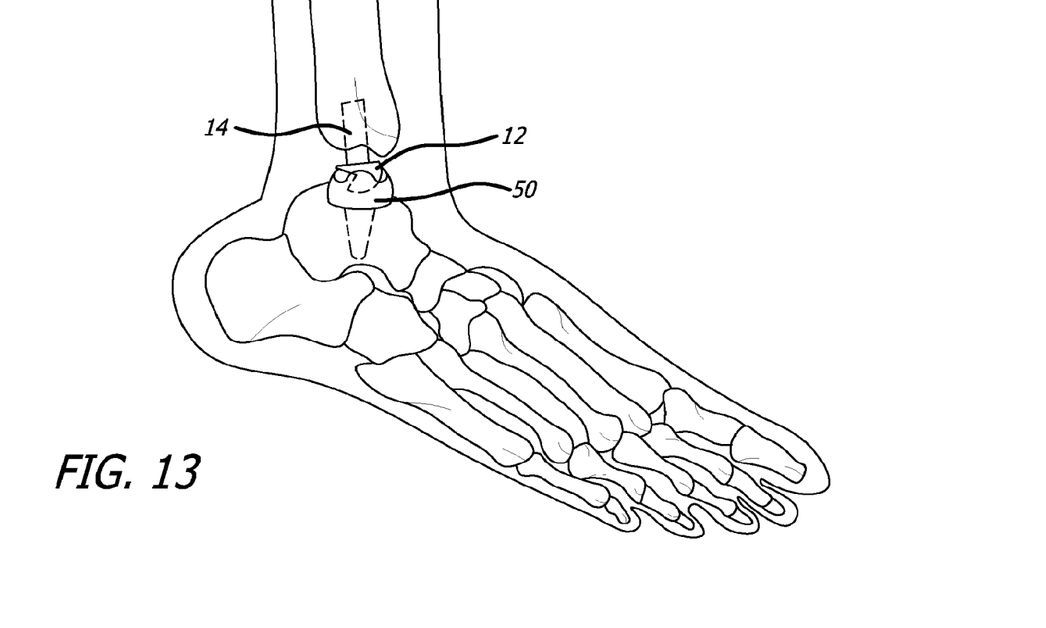
FIG. 13 illustrates one embodiment of a ball and socket assembly as a joint prosthesis for an ankle joint.

As shown in FIG. 13, the use of the hook-in ball 10 and socket 50 assembly is contemplated as an ankle joint prosthesis. The ankle joint prosthesis shown in FIG. 13 has similar benefits to the joint prostheses shown in FIGS. 10-12. Additionally, the hook-in ball 10 and socket 50 can provide a better range of motion as compared to other ankle prostheses.

Figure 14:
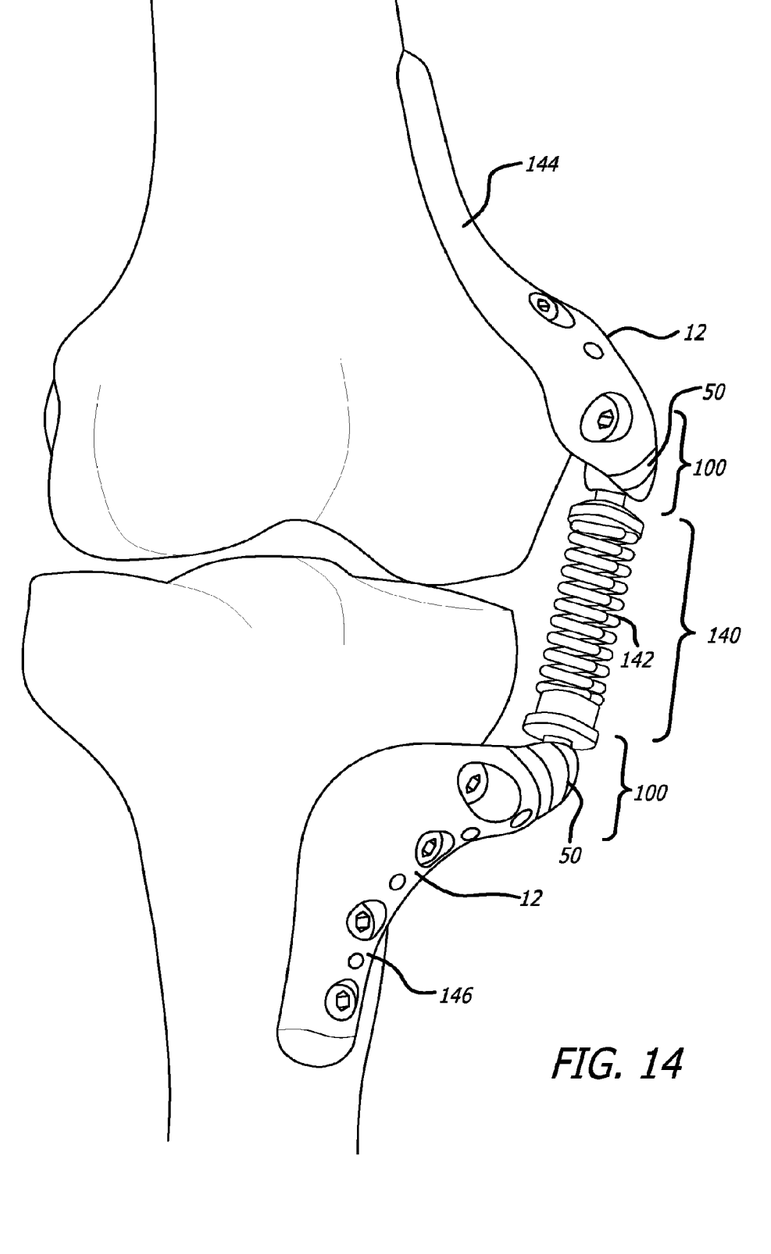
FIG. 14 illustrates one embodiment of a ball and socket assembly used in an extra-articular mechanical energy absorbing system.

FIG. 14 illustrates the use of the hook-in ball 10 and the socket 50 assembly as joints within an extra-articular mechanical energy absorbing or manipulating system 140. According to one embodiment, the implantable system 140 is composed of an absorber 142 that spans a joint (e.g., the knee as shown in FIG. 14) and off-loads forces at the joint. The ends of the absorber 142 are multi-dimensionally, pivotally coupled to base components 144, 146 via the hook-in ball and socket assembly 100. The assembly 100 allows the absorber 142 to track the natural movement of joint (e.g., knee joint).

The hook-in ball and assembly socket assembly 100 shown in FIGS. 10-14 are low-profile connections that may be used in various parts of the body anatomy. The assembly 100 is designed to provide maximum load contact area (between the ball component surface and the socket cavity) thereby improving wear performance of the joint. Additionally, the assembly 100 is self-lubricating when implanted within the body as the structure is exposed to body fluids and in a lipid rich environment (i.e., in contact with or exposed to fatty tissue), thereby further improving wear performance of the joint. Accordingly, it is contemplated that the components of the assembly do not need to be frequently replaced.

As those skilled in the art will appreciate, the disclosed embodiments of the hook-in ball and socket assemblies may be combined to form a joint for various contemplated purposes. Additionally, the pivot connections disclosed herein may be used in mechanical arts requiring a connection that allows for relative angular movement between two components.

The various embodiments described above are provided by way of illustration only and should not be construed to limit the disclosed embodiments. Accordingly, certain elements and structures of one approach can be substituted for or added to complement other approaches. Those skilled in the art will readily recognize various modifications and changes that may be made to the disclosed embodiments without departing from the true spirit and scope of the claimed invention, which is set forth in the following claims.

What is claimed is:

1. A ball and socket assembly, comprising:
 a generally non-deformable ball component having a surface forming a portion of a sphere;
 an elongated shaft coupled to said ball component;
 a single piece, generally non-deformable socket component, the socket including a bearing surface defining a contour assuming a portion of a sphere and an opening that is smaller than the diameter of the ball component in at least one diameter;
 wherein the ball component includes a cavity formed therein; and
 wherein the assembly includes a filler component sized to fit the cavity.

2. The assembly of claim 1, wherein the opening of the socket component is defined by substantially non-deformable components with no separation line in the portion of the socket component contacting the ball component when the ball component and socket component experience loads during use.

3. The assembly of claim 1, wherein the ball component and socket component are formed to provide a load surface area with no separation line in the portion of the socket component contacting the ball component when the ball component and socket component experience loads during use.

4. The assembly of claim 1, wherein the cavity is defined by a volume that is removed to allow insertion of the ball component through the opening.

5. The assembly of claim 1, wherein the ball component is inserted into the opening of the socket component in a first orientation and is constrained to operate in various orientations distinct from the first orientation.

6. The assembly of claim 1, wherein the socket component is formed of a single piece.

* * * * *